(12) United States Patent
Wilder-Smith et al.

(10) Patent No.: US 8,396,530 B1
(45) Date of Patent: Mar. 12, 2013

(54) METHOD FOR BIOSENSOR USAGE WITH PRESSURE COMPENSATION

(71) Applicant: Affectiva, Inc., Waltham, MA (US)

(72) Inventors: Oliver Orion Wilder-Smith, Holliston, MA (US); Rosalind Wright Picard, Newtonville, MA (US); Tao Zhang, Natick, MA (US)

(73) Assignee: Affectiva, Inc., Waltham, MA (US)

( * ) Notice: Subject to any disclaimer, the term of this patent is extended or adjusted under 35 U.S.C. 154(b) by 0 days.

(21) Appl. No.: 13/674,325

(22) Filed: Nov. 12, 2012

Related U.S. Application Data

(63) Continuation of application No. 12/905,636, filed on Oct. 15, 2010, now Pat. No. 8,311,605, which is a continuation-in-part of application No. 12/840,074, filed on Jul. 20, 2010.

(60) Provisional application No. 61/252,337, filed on Oct. 16, 2009.

(51) Int. Cl.
*A61B 5/04* (2006.01)
(52) U.S. Cl. ......... 600/382; 600/386; 600/388; 600/393
(58) Field of Classification Search .................. 600/372, 600/382, 384, 386, 388, 390, 393
See application file for complete search history.

(56) References Cited

U.S. PATENT DOCUMENTS

| | | | |
|---|---|---|---|
| 5,897,505 A | 4/1999 | Feinberg et al. | |
| 5,964,719 A | 10/1999 | Costello et al. | |
| 6,415,176 B1 | 7/2002 | Scheirer et al. | |
| 6,491,647 B1 * | 12/2002 | Bridger et al. | 600/585 |
| 7,020,508 B2 | 3/2006 | Stivoric | |
| 7,285,090 B2 | 10/2007 | Stivoric | |
| 7,753,846 B2 | 7/2010 | Park et al. | |
| 8,140,143 B2 | 3/2012 | Picard et al. | |
| 2002/0032386 A1 | 3/2002 | Sackner | |
| 2002/0038092 A1 | 3/2002 | Stanaland | |
| 2002/0198574 A1 | 12/2002 | Gumpert | |
| 2003/0004424 A1 | 1/2003 | Birnbaum | |
| 2003/0117651 A1 | 6/2003 | Matraszek | |
| 2004/0039254 A1 | 2/2004 | Stivoric | |
| 2004/0073121 A1 | 4/2004 | Sun | |
| 2004/0133081 A1 | 7/2004 | Teller | |
| 2004/0152957 A1 | 8/2004 | Stivoric | |
| 2005/0107655 A1 | 5/2005 | Holzner | |

(Continued)

FOREIGN PATENT DOCUMENTS

| | | |
|---|---|---|
| EP | 1886707 A1 | 2/2008 |
| WO | WO2009023937 A1 | 2/2009 |

(Continued)

OTHER PUBLICATIONS

Bruyker et al. Thermostatic control for temperature compensation of a silicon pressure sensor Jul. 2, 2009.*

(Continued)

*Primary Examiner* — Michael Peffley
*Assistant Examiner* — Brian M Antiskay
(74) *Attorney, Agent, or Firm* — Adams Intellex, PLC

(57) ABSTRACT

A biosensor is described which can obtain physiological data from an individual. The biosensor may collect electrodermal activity, skin temperature, and other information. The biosensor may be attached to the body through the use of a garment which may be fastened in multiple locations on the human body. The biosensor includes compensation for electrodermal activity measurements based on the amount of pressure applied to the electrodes that are in contact with the skin. As pressure is increased the electrodermal activity values typically increase. By compensating for the influence that pressure changes have on electrodermal activity, more accurate analysis of physiology and therefore mental state analysis may be performed.

20 Claims, 8 Drawing Sheets

U.S. PATENT DOCUMENTS

| | | |
|---|---|---|
| 2006/0069319 A1 | 3/2006 | Elhag |
| 2006/0149146 A1* | 7/2006 | Schmidt et al. ............... 600/372 |
| 2006/0264730 A1 | 11/2006 | Stivoric |
| 2006/0293608 A1 | 12/2006 | Rothman |
| 2007/0208233 A1 | 9/2007 | Kovacs |
| 2007/0299325 A1 | 12/2007 | Farrell et al. |
| 2008/0058652 A1* | 3/2008 | Payne ........................... 600/488 |
| 2008/0161654 A1 | 7/2008 | Teller |
| 2008/0161655 A1 | 7/2008 | Teller |
| 2008/0167536 A1 | 7/2008 | Teller |
| 2008/0167537 A1 | 7/2008 | Teller |
| 2008/0167538 A1 | 7/2008 | Teller |
| 2008/0167539 A1 | 7/2008 | Teller |
| 2008/0171919 A1 | 7/2008 | Stivoric |
| 2008/0171920 A1 | 7/2008 | Teller |
| 2008/0171921 A1 | 7/2008 | Teller |
| 2008/0171922 A1 | 7/2008 | Teller |
| 2008/0214089 A1 | 9/2008 | Vermac |
| 2008/0275309 A1 | 11/2008 | Stivoric |
| 2008/0287751 A1 | 11/2008 | Stivoric |
| 2009/0069642 A1 | 3/2009 | Gao |
| 2009/0076340 A1 | 3/2009 | Libbus et al. |
| 2009/0177068 A1 | 7/2009 | Stivoric |

FOREIGN PATENT DOCUMENTS

| | | |
|---|---|---|
| WO | WO2009036150 A2 | 3/2009 |

OTHER PUBLICATIONS

International Search Report dated Jul. 20, 2010 for PCT/US2010/031115.
"GoWear display User Guide," by BodyMedia.
"Quick Start!" for BodyMedia Armband.
"GoWear fit armband User Guide," by BodyMedia.

* cited by examiner

METHOD FOR BIOSENSOR USAGE WITH PRESSURE COMPENSATION

RELATED APPLICATIONS

This application is a continuation of U.S. patent application "Biosensor with Pressure Compensation" Ser. No. 12/905,636 currently U.S. Pat. No. 8,311,605, filed Oct. 15, 2010. U.S. patent application "Biosensor with Pressure Compensation" Ser. No. 12/905,636, filed Oct. 15, 2010 claims the benefit of the U.S. provisional patent application "Biosensor Module" Ser. No. 61/252,337, filed Oct. 16, 2009 and is also a continuation-in-part of U.S. patent application "Biosensor Module with Automatic Power On Capability" Ser. No. 12/840,074, filed Jul. 20, 2010 and is further related to patent application "Biosensor Module with Leadless Contacts" Ser. No. 12/905,560, filed Oct. 15, 2010. U.S. patent application "Biosensor Module with Automatic Power On Capability" Ser. No. 12/840,074, filed Jul. 20, 2010 claims the benefit of the U.S. provisional patent application "Biosensor Module" Ser. No. 61/252,337, filed Oct. 16, 2009. Each of the foregoing applications is hereby incorporated by reference in their entirety.

FIELD OF INVENTION

This application relates generally to physiological sensors and more particularly to improved accuracy biosensors through pressure compensation.

BACKGROUND

Physiological and other information on individuals can be extremely useful when evaluating health and activity. Physiological information may include electrodermal activity (EDA) also known as skin conductance or galvanic skin response (GSR). Physiological information may further include skin temperature, heart rate, heart rate variability, and various other aspects of the human body's condition. Useful information may also be found through tracking movements such as those that may be collected through accelerometer readings. All these readings and other information may be collected to evaluate the health of an individual, to diagnose numerous health problems, and to track physical or exercise activity.

Further, the physiological and other data collected can be useful in evaluating health or other information on an individual. Many of the physiological readings and other information may be obtained through a biosensor attached to a human body. Biosensors have been either stationary or portable. Historically these biosensors, however, have been cumbersome and difficult to use. The presence of a cumbersome biosensor could even impact the user's readings, simply by the awareness of the person to the biosensor.

There remains a need for improved monitoring of physiological information through improved biosensor modules.

SUMMARY

Analysis of physiological readings from a person can be key in evaluating health or even the mental state of an individual. A biosensor may be provided to monitor motion and physiological readings for an individual.

An apparatus is disclosed for measuring physiology comprising: a pair of electrodes; one or more pressure sensing devices attached to one or more of each of the pair of electrodes; circuitry to evaluate electrodermal activity of skin to which the pair of electrodes contacts; and circuitry to compensate electrodermal activity evaluation based on force applied to pair of the electrodes. The one or more pressure sensing devices may include one of a group comprising force sensitive resistors, piezoelectric devices, piezoelectric polymers, and pressure sensitive gels. The circuitry to evaluate electrodermal activity may include a processor and one of software and firmware. The circuitry to compensate electrodermal activity may include a processor and one of software and firmware. In embodiments, the apparatus of claim 1 may further comprise circuitry to correct electrodermal activity evaluations based on temperature of the skin. In some embodiments, the apparatus may further comprise circuitry to correct electrodermal activity evaluations based on sensed humidity. In embodiments, the apparatus may further comprise a garment to hold the pair of electrodes against a body. The garment may be suitable to be worn in multiple locations on the body. In embodiments, the apparatus may further comprise circuitry to evaluate skin temperature. The apparatus may also further comprising circuitry to compensate skin temperature evaluation based on the force applied to the electrodes.

In some embodiments, a method for measuring physiology may comprise: capturing electrodermal activity readings from a body to which electrodes are in contact with skin; collecting pressure information on an amount of pressure applied to the electrodes which are in contact with the skin; and compensating the electrodermal activity readings based on the pressure information which was collected. The pressure information may be collected using one of a group comprising force sensitive resistors, piezoelectric devices, piezoelectric polymers, pressure sensitive materials, and pressure sensitive gels. The compensating may be accomplished using one of a group comprising circuitry, a processor, software and firmware. The compensating may be accomplished real time as the electrodermal activity readings are captured. In embodiments, the method may further comprise correcting electrodermal activity evaluations based on temperature of the skin. The method may further comprise correcting electrodermal activity evaluations based on sensed humidity. The method may include evaluating skin temperature. The method may further comprise compensating skin temperature evaluation based on force applied to the electrodes.

In some embodiments, a computer program product embodied in a non-transitory computer readable medium that, when executed, may perform steps of: capturing electrodermal activity readings from a body to which electrodes are in contact with skin; collecting pressure information on an amount of pressure applied to the electrodes which are in contact with the skin; and compensating the electrodermal activity readings based on the pressure information which was collected. In embodiments, a system for measuring physiology may comprise: a sensor including a pair of electrodes and one or more pressure sensing devices; and a processor attached to the sensor wherein the processor is configured to perform steps of: capturing electrodermal activity readings from skin of a body to which the pair of electrodes are in contact; collecting pressure information on an amount of pressure applied to the electrodes with the one or more pressure sensing devices; and compensating the electrodermal activity readings based on the pressure information which was collected.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

The present disclosure provides a description of various apparatus, methods, and systems associated with sensing physiological information related to an individual. There is a need for an improved sensor of this type of information. A biosensor may obtain information on electrodermal activity, skin temperature, accelerometer readings, heart rate, heart rate variability, blood pressure, blood sugar, and other information about an individual. The collected information may be used to monitor the health of an individual and evaluate mental states for the individual. Monitoring such mental states can be useful for both therapeutic and business purposes. A mental state may be an emotional state or a cognitive state. Examples of emotional states include happiness or sadness. Examples of cognitive states include concentration or confusion. Thus, mental states may include frustration, confusion, disappointment, hesitation, cognitive overload, focusing, being engaged, attending, boredom, exploration, confidence, trust, delight, and satisfaction. Many mental states, such as engagement, excitement, confusion, concentration, and worry, may be identified to aid in the understanding of an individual and their response to certain stimuli such as an advertisement, walking through a store, interacting with a web site, a movie, a movie trailer, a product, a computer game, a video game, or consuming a food.

Figure 1:
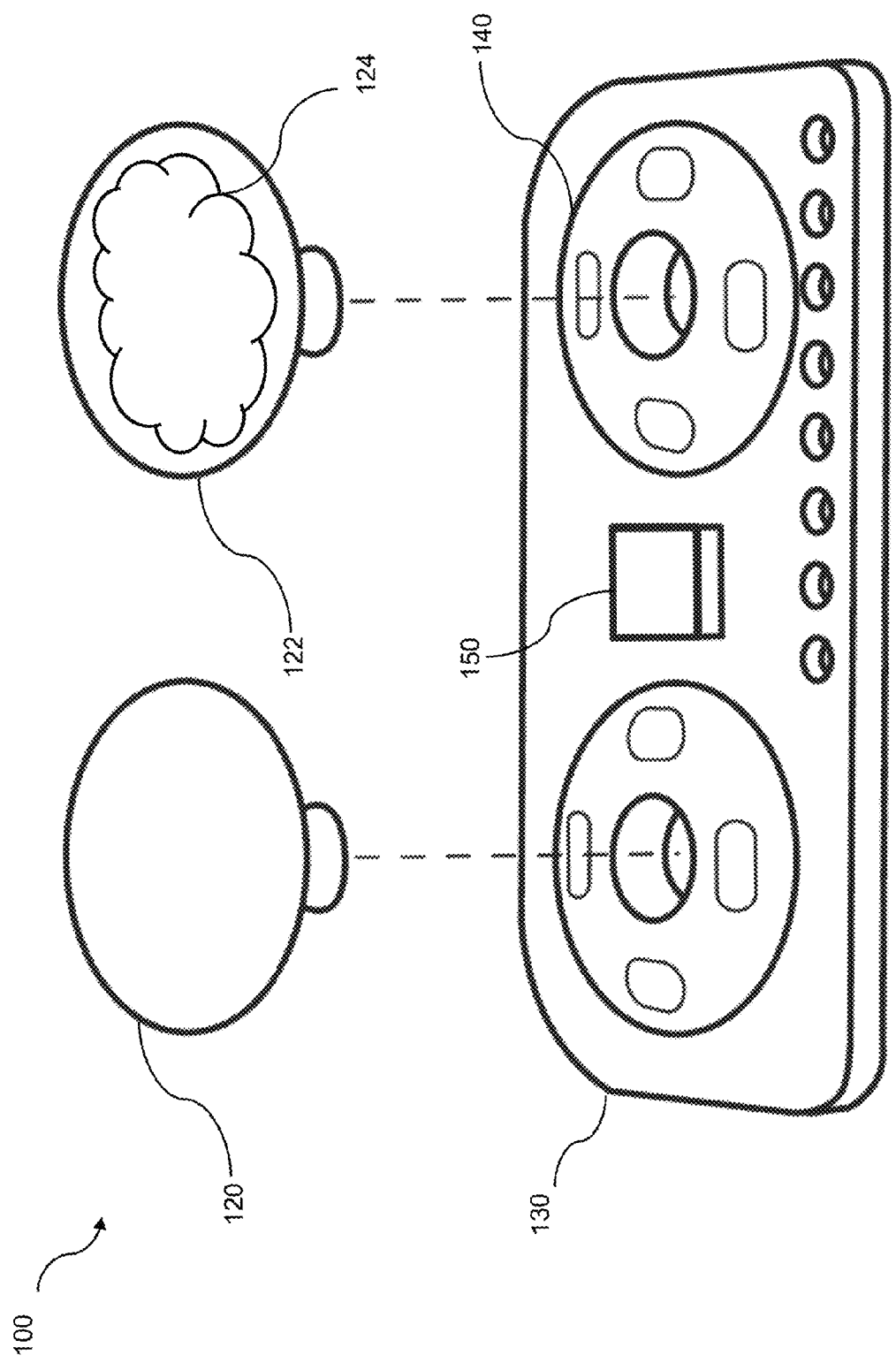
FIG. 1 is a diagram of a pair of replaceable electrodes that snap.

FIG. 1 is a diagram of a pair of replaceable electrodes that snap into place. A system 100 may be part of wearable apparatus for monitoring physiological information for an individual. The system 100 includes a plurality of replaceable electrodes 120 and 122 electrically connected to a circuit board wherein the electrodes have a leadless attachment to the sensor. Historically, the place where leads attach is the main source of breakage in traditional sensors and this new design eliminates that breaking point. In some embodiments, the plurality of replaceable electrodes comprises two electrodes. These electrodes may be considered contacts, which provide contact from the biosensor to the skin. The electrodes 120 and 122 may attach to circuit board 130 which is part of the physiological sensor. The plurality of electrodes 120 and 122 may be snap-in electrodes. For example, the electrode 122 may snap into an electrode receiver 140. The snap-in electrode 122 may include a solder-in snap receiver that is soldered to the circuit board 130. In this manner, the electrodes 120 and 122 may have a leadless attachment, which includes no wires external to the sensor and yet the plurality of electrodes are electrically connected to the circuit board. The electrode receiver 140 may be suitable for robotic assembly using a robotic pick and place machine. The electrode receiver 140 may be shaped with a flat surface such that a suction device on a robot may be used to pick up the receiver. Alternatively, an additional shape may be temporarily attached to the receiver, such as a piece of plastic that has a flat surface for picking up with a suction device on a robot. The additional shape may be broken off or removed once the receiver is placed on the apparatus for assembly.

The replaceable electrodes may be interchangeable with other types of electrodes. For example, the electrodes may be sanitary and may be dry or gelled. By way of example, a gel 124 may be applied to the electrode 122. The sensor may indicate electrodermal activity, skin temperature, heart rate, or heart rate variability. Additionally, an accelerometer 150 may be included in the sensor to capture motion related readings. Accelerometer readings can be quite useful to determine the activity of the individual and even what type of activity in which the individual is involved.

Figure 2:
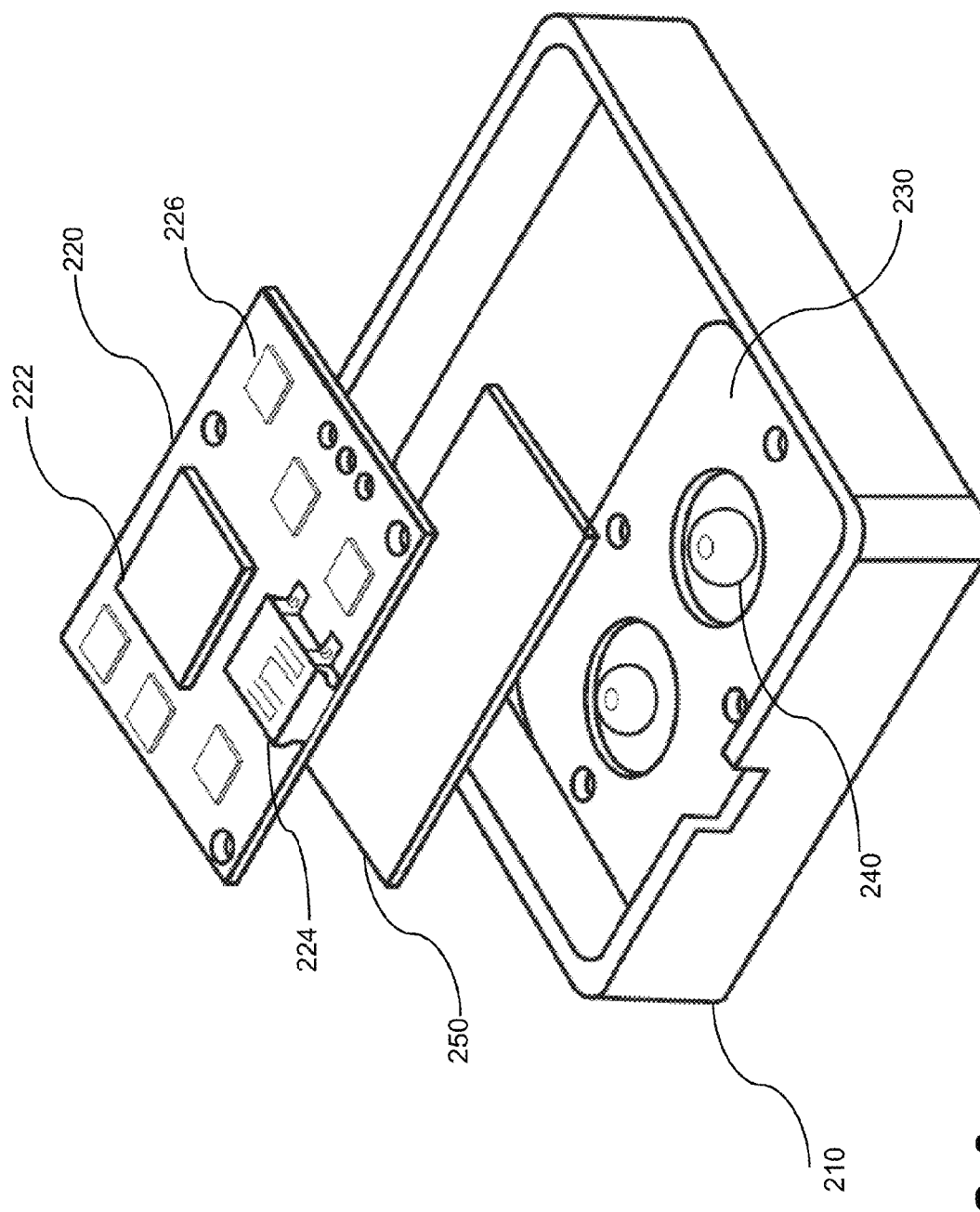
FIG. 2 is a diagram of an exploded sensor module.

FIG. 2 is a diagram of an exploded sensor module. The sensor module 210 may include a circuit board 220, thermal tape 230, and a snap receiver 240. The circuit board 220 may be incorporated as part of the sensor module. The circuit board may include a processor 222, a connection port 224, and memory 226. The circuit board 220 may be rigid or may be flexible. In some embodiments the sensor module may be rigid and be formed from hard plastic. In other embodiments, the sensor module may be formed from a flexible material that adapts to the shape of the skin. When the module is flexible, it is advantageous for the circuit board 220 to be flexible as well. The communication port 224 may be a universal serial bus (USB) port. The USB port may be a standard USB port, a mini-USB port, or a micro-USB port. The communication port 224 may be used for downloading readings that were sensed by the biosensor and stored in a memory 226. Data from the biosensor may be collected for several hours or even more than a day and stored in the memory 226. One or more memory modules may be attached to the circuit board 220. The storage memory 226 may be non-volatile memory such as Flash, magnetoresistive random access memory (MRAM), ferroelectric random access memory (FeRAM), or phase change memory. The storage memory 226 may also include some volatile memory such as SRAM or DRAM. The storage memory 226 may further be used to store configuration information for the biosensor module 210. The memory 226 may also be used to store instructions for the processor 222. Physiological readings that are stored in the memory 226 may be downloaded later in time after the sensor has been removed from the body. Alternatively, physiological readings may be streamed through a wireless connection for storage and analysis in a computer system. In yet another embodiment, physiological readings may be stored in memory and then read from memory through wireless burst transmissions at specific times or through a given wireless protocol.

A circuit board 230 may include one or more snap receivers 240 into which electrodes can be snapped. The circuit board 230 is the back side view of circuit board 130 from FIG. 1. Likewise, the snap receiver 240 is the backside view of the electrode receiver 140 from FIG. 1. In some embodiments the snap receiver 240 is a parallel spring connector. In some embodiments the snap receiver 240 may be electrically connected to the circuit board 220 through a wire, which is soldered to the snap receiver 240, and the circuit board 220 respectively. Alternatively, the snap receiver 240 may be electrically connected to the circuit board 220 through a direct metal connection that occurs when the sensor module 210 is assembled. In some embodiments the circuit board 230 may be considered a first circuit board and the circuit board 220 may be considered a second circuit board. In some embodiments the circuit board 220 may be considered a mother board while circuit board 230 may be considered a daughter board. In embodiments, the first circuit board and the second circuit board may be combined so that a single circuit board is used in the sensor module.

A piece of thermal tape 250 for thermal connection between the electrodes and the circuit board may be provided wherein the thermal connection provides for measurement of skin temperature. The thermal tape 250 may cover the snap receivers 240 and provide thermal connection to a thermal sensor on the backside of the circuit board 220. In some embodiments, the thermal tape 250 will be an electrically insulating material where a wire will electrically connect the snap receiver 240 to the circuit board 220. This electrical connection will be used for electrodermal activity readings or other physiological information. In some embodiments, thermal epoxy may be used for thermal connection between the electrodes and the circuit board 220 wherein the thermal connection provides for measurement of skin temperature.

The circuit board 220 may include circuitry to evaluate electrodermal activity of skin to which the pair of electrodes contacts. Electrodermal activity readings can be affected by an amount of pressure that the electrodes apply to the skin. The circuit board 220 may include circuitry to compensate electrodermal activity evaluation based on force applied by the pair of electrodes. The circuitry to evaluate electrodermal activity may include a processor 220 and software or firmware. The code of the software or firmware may be stored on the memory 226 or in the processor 222 with on-chip memory. The circuitry to compensate electrodermal activity may include a processor, a field programmable gate array (FPGA), and one of software and firmware. Circuitry and sensors may be included to evaluate skin temperature. The circuitry may also correct electrodermal activity evaluations based on temperature of the skin. Further, circuitry and sensors may be included to correct electrodermal activity evaluations based on sensed humidity. Circuitry may also be included to compensate skin temperature evaluation based on the force applied to the electrodes. The compensating may be accomplished using circuitry, a processor, software or firmware.

Figure 3:
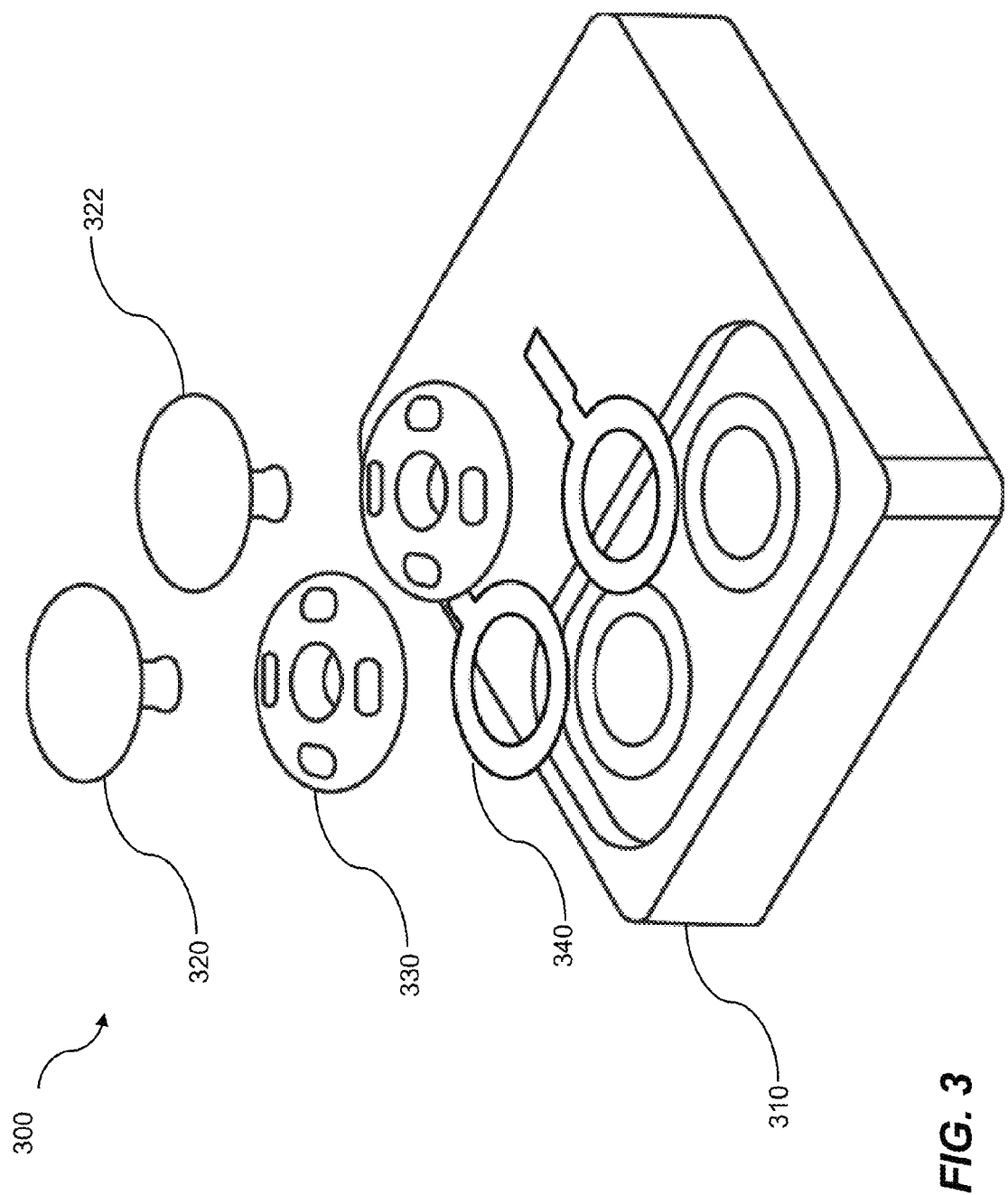
FIG. 3 is an exploded diagram showing electrodes and a sensor module.

FIG. 3 is an exploded diagram showing electrodes and a sensor module. The system 300 includes a pressure sensing device 340 attached to an electrode 320. The electrode 320 may snap into an electrode receiver 330. The electrode receiver 330 may be soldered into a circuit board and be electrically connected so that electrodermal activity and other physiological readings may be obtained. The system 300 may include a sensor housing 310 which contains circuitry for compensating electrodermal activity evaluations based on a measurement of force applied to the electrode 320. The pressure sensing device may comprise a force sensitive resistor 340. A plurality of replaceable electrodes 320 and 322 may be electrically connected to the circuit board wherein the electrodes have a leadless attachment to the sensor. The replaceable electrodes 320 and 322 may be interchangeable with other electrodes and other types of electrodes. The leadless attachment may include no wires external to the sensor. The system 300 may include an apparatus for measuring physiology comprising a pair of electrodes 320 and 322 and one or more pressure sensing devices 340 attached to one or more of each of the pair of electrodes 320 and 322. The one or more pressure sensing devices 340 collects the pressure information using force sensitive resistors, piezoelectric devices, piezoelectric polymers, microelectromechanical systems (MEMS), or pressure sensitive gels. In embodiments, sensors may be used and sensor readings may be obtained from a human while in other embodiments sensor readings may be obtained from an animal. Throughout this disclosure it should be understood that sensor readings obtained for a human could similarly be accomplished for a monkey, chimpanzee, dog, guinea pig, rat, or other animal. Thus a body may refer to a human body or an animal body, to which a sensor is attached.

Figure 4:
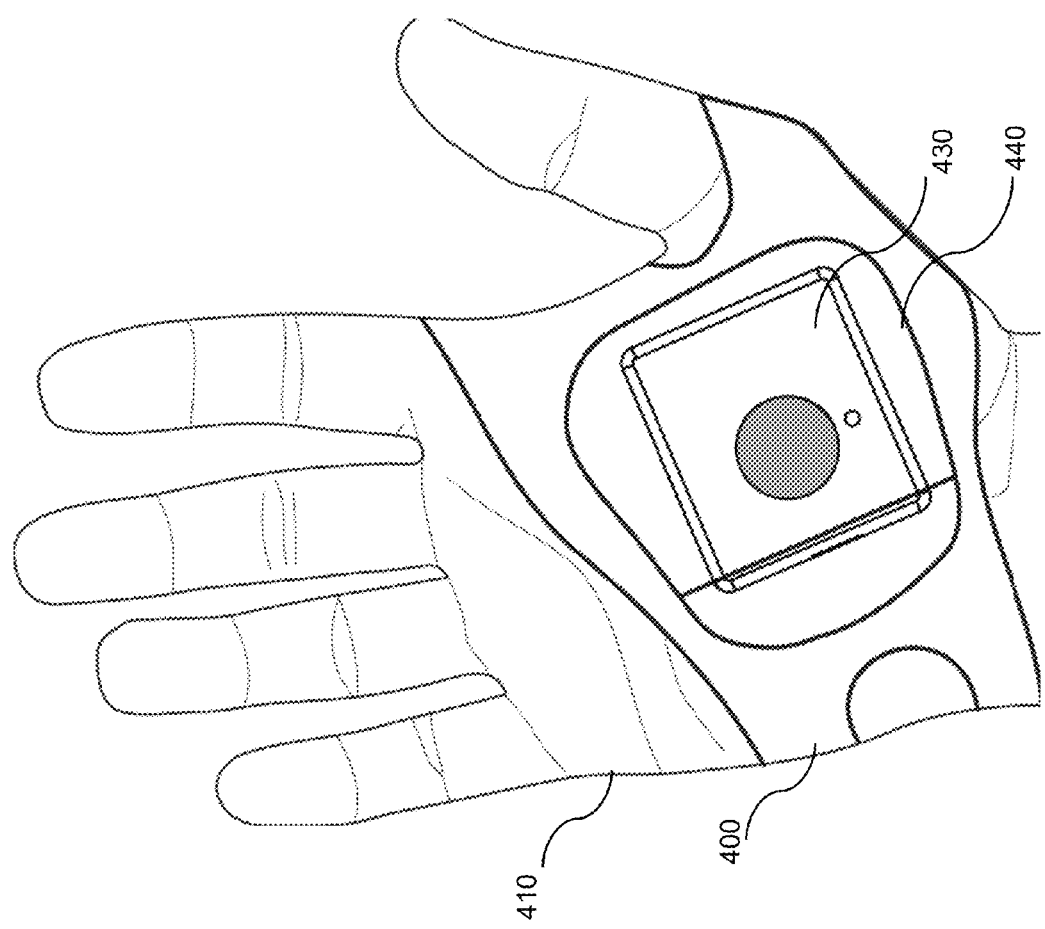
FIG. 4 is a diagram of a garment and sensor on a hand.

FIG. 4 is a diagram of a garment and sensor on a hand. A hand 410 is shown with a garment 400 wrapped around the hand. In various embodiments the garment may be wrapped around various other parts of a body. A physiological sensor 430 exists within a pouch of the garment 420. A cutaway view 440 of the garment 400 is provided so that the sensor can be noted. The sensor may be used to detect one or more of electrodermal activity, skin temperature, accelerometer readings, heart rate, and heart rate variability as well as various other physiological conditions. Thus, in embodiments, there is an attachment means for attaching the sensor to the body. The attachment means may be one of a garment, an adhesive, and a strap. Thus, a wearable apparatus may be included for monitoring physiological information for an individual comprising a garment 400 adapted to be worn on a body along with a sensor 430, attached to the garment 400, which may indicate at least one of electrodermal activity, skin temperature, heart rate, and heart rate variability.

Figure 5:
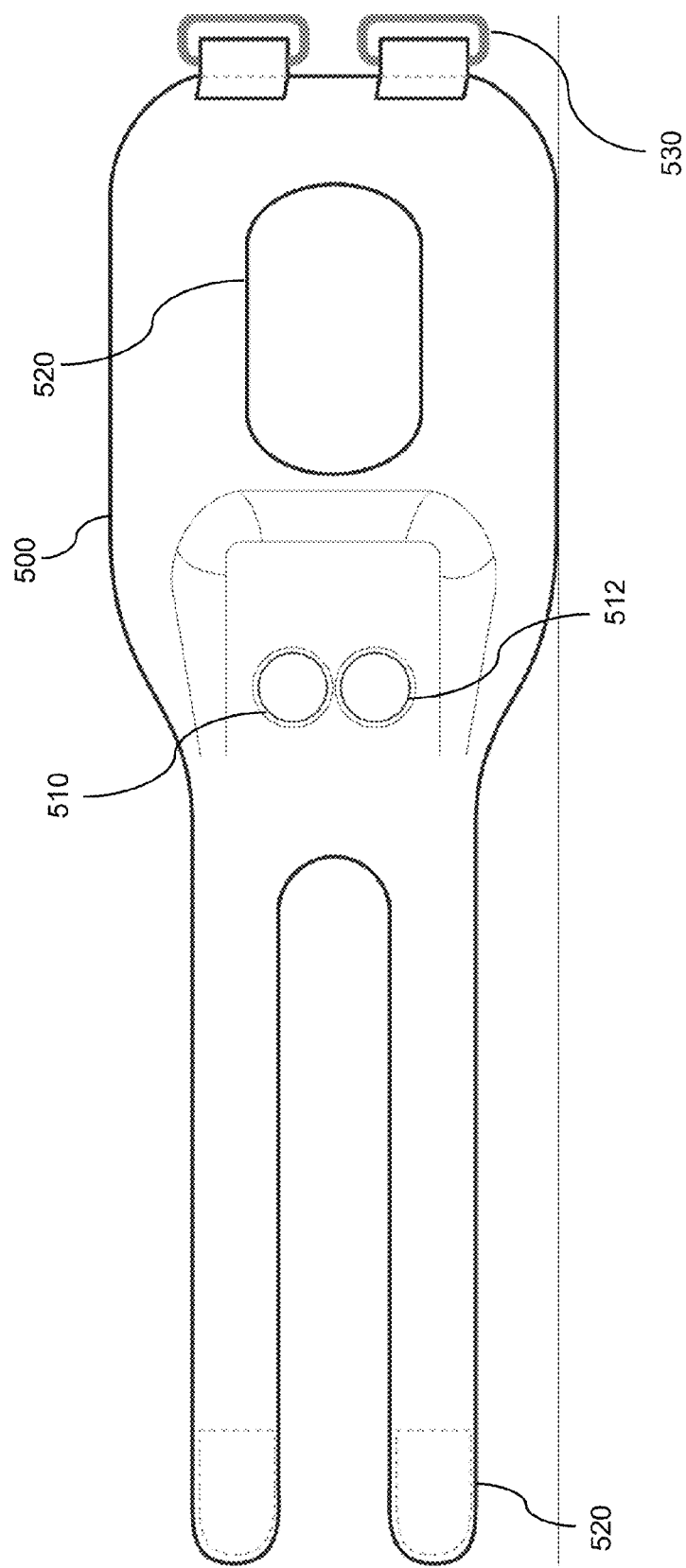
FIG. 5 is a diagram of a garment with protruding electrodes.

FIG. 5 is a diagram of a garment with protruding electrodes. The garment 500 may include a hole 520 for a person's thumb to stick through. The garment may include one or more straps 520 which are secured around a hand or wrist to one or more loops 530. The strap 520 may be secured by Velcro™, a button, snap, clasp, hook, or a belt prong through an eyelet. FIG. 5 shows the garment 500 which is the backside of the garment 400 shown in FIG. 4. The garment 500 has two holes 510 and 512 that allow electrodes from the sensor to protrude through and contact skin. Thus a garment 500 is provided to hold the pair of electrodes against a body.

Figure 6B:
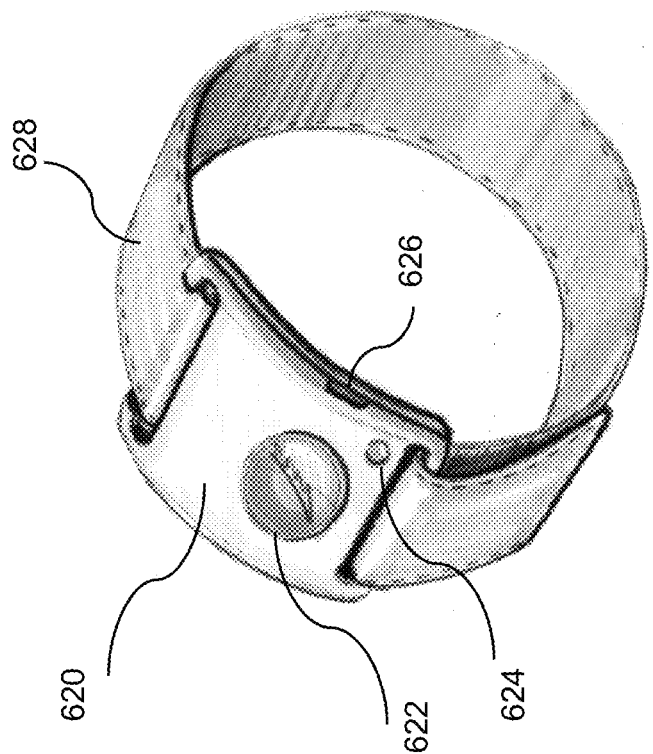
FIG. 6B is a diagram of a sensor on a wristband.
Figure 6A:
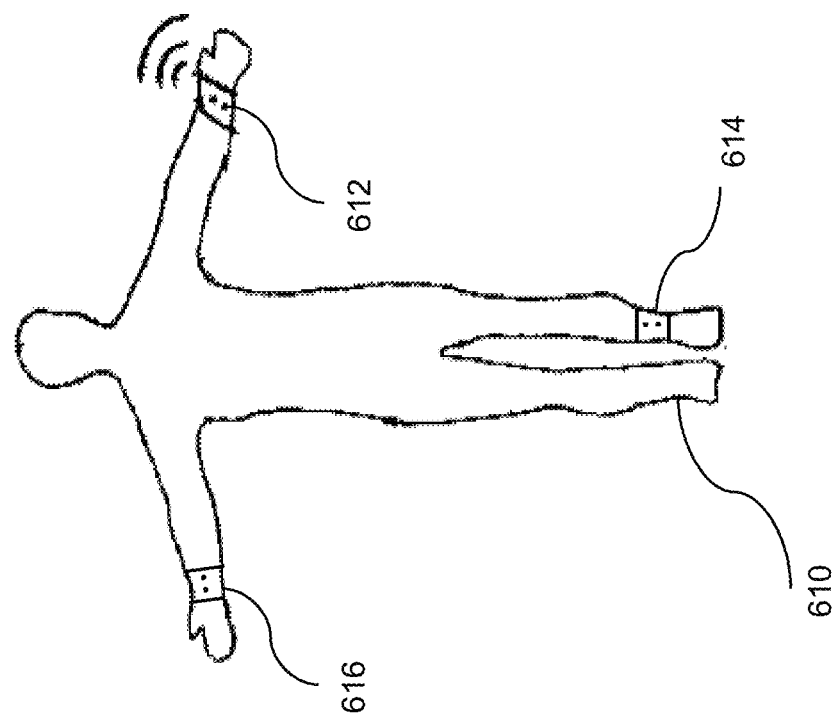
FIG. 6A is a diagram of sensors attached to a human body.

FIG. 6A is a diagram of sensors attached to a human body. A body 610 for a person is shown. A biosensor 612 may be attached to the body 610. The biosensor 612 may be attached to a wrist, to a hand, the head, or to some other part of the body 610. By way of example, a biosensor 614 is shown attached to an ankle and a biosensor 616 is shown attached to the other wrist. The biosensor 612 may be attached by a wristband, a garment, a sleeve, an adhesive, or some other means. The garment may be suitable to be worn in multiple locations on the human body.

The biosensor 612 may store data collected from the person. The data collected may include electrodermal activity readings, accelerometer readings, skin temperature readings, heart rate, heart rate variability, or other information. All of these readings may be considered physiological data. Alternatively, the accelerometer readings may be considered activity measurements and the electrodermal activity, skin temperature, and heart rate readings may be considered physiological data. The various data collected may later be read through a USB or other communication port. Alternatively, a wireless connection to the biosensor may be used to continuously or occasionally burst download the collected data.

FIG. 6B is a diagram of a sensor on a wristband. A biosensor 620 is shown with a button 622, an LED 624, a USB port 626, and a wristband 628. The biosensor 620 may be used for collecting electrodermal activity readings, accelerometer readings, skin temperature readings, heart rate, heart rate variability, or other information. The biosensor 620 may have two electrodes on the side of the biosensor 620 toward the skin. These electrodes may be used to measure electrodermal activity. One or more electrodes may also be used to measure skin temperature. The button 622 may be used to turn off the biosensor 620, turn on the biosensor 620, or to mark an event of interest. By pressing the button 622, the user may record a point of interest for the data being collected. Then the data can be later analyzed recognizing the point of interest marked along with the associated data.

The LED 624 may blink when the biosensor 620 turns on. The LED 624 may also be used to indicate that the biosensor 620 is continuing to operate or the state of the battery. The USB port 626 may be on one of the sides or top or bottom of the biosensor 620. Numerous types of ports may be used including a USB port, a mini-USB port, a micro-USB port or other type of connection. These connections may be used to charge a battery within the biosensor 620 and may be used to store data or instruction on the biosensor 620 or to read data collected by the biosensor 620. The wristband 628 may be used to secure the biosensor to an individual. Velcro™ may be used to secure the wristband 628. Alternatively, a clasp, button, snap, or other means of attaching the wristband may be used. The attachment means may allow attachment of the sensor to multiple locations on the human body.

The shape of biosensor 620 is shaped in a curve to be adapted for use on a person's wrist. Other shapes or biosensors may be used such as a biosensor that is flat on both the top and bottom side. Other apparatus may be used for securing the biosensor to the person's body. For instance a cloth sleeve may be adapted to fit around a wrist. The cloth sleeve may be formed from a stretchable fabric for ease of use and comfort. The cloth sleeve may be secured around the wrist by Velcro™, snaps, a zipper, or buttons. The cloth sleeve may have a pocket within which a biosensor fits. The pocket may be securable with a flap that has a snap, zipper, buttons, or Velcro™ on it. The biosensor may also be adapted to fit another part of the body. The cloth sleeve or other securing device may be adapted to fit the shape of the other part of the body.

Figure 7:
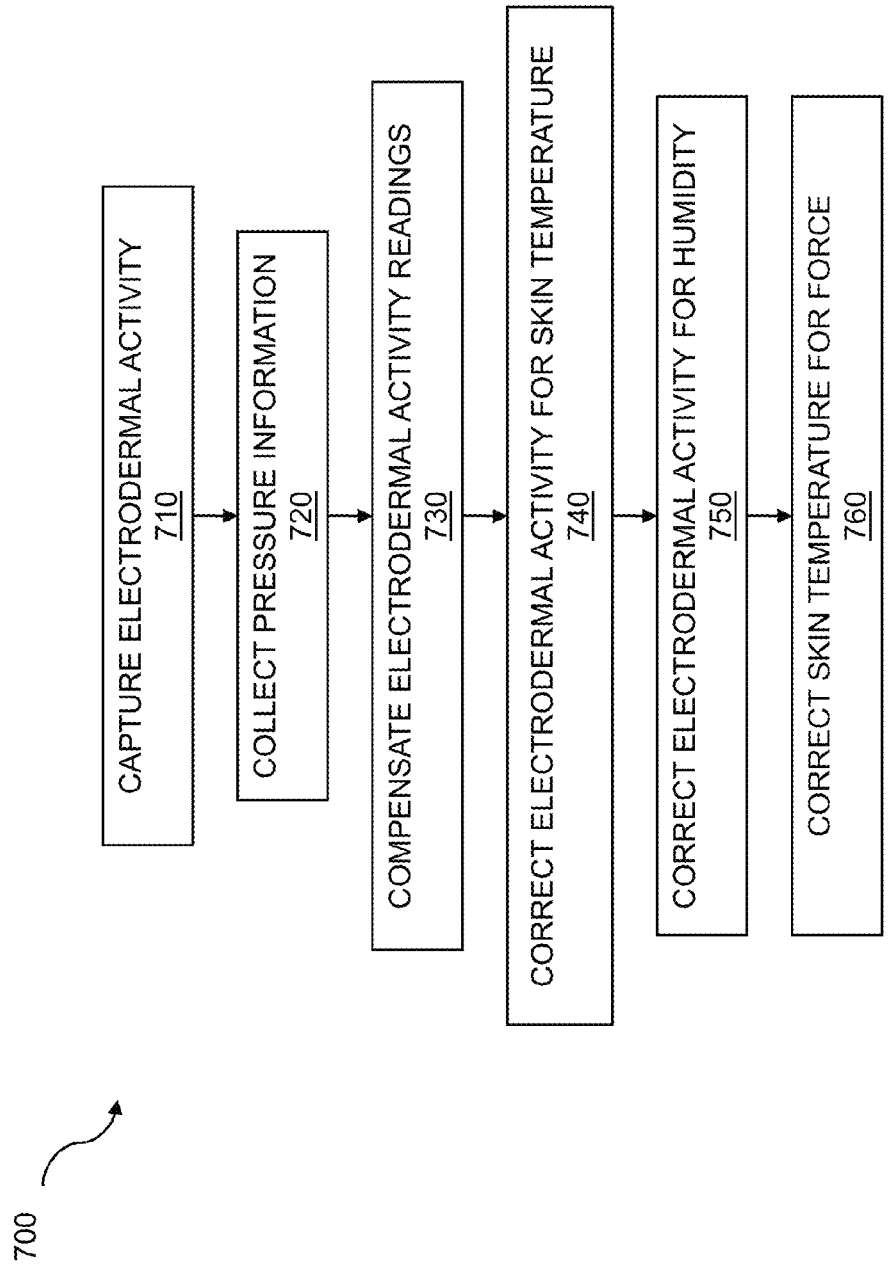
FIG. 7 is a flowchart compensating EDA for pressure.

FIG. 7 is a flowchart compensating EDA for pressure. The flow 700 for a method for measuring physiology begins with capturing electrodermal activity readings 710 from a body to which electrodes are in contact with skin. The flow 700 may continue with collecting pressure information 720 on an amount of pressure applied to the electrodes which are in contact with the skin. The pressure information collection may occur simultaneously with the electrodermal activity capture. Additionally, in some embodiments, the pressure information collection may occur before the electrodermal activity information is captured. In some cases pressure changes may precede detectable changes in electrodermal activity. The flow 700 may continue with compensating the electrodermal activity readings 730 based on the pressure information that was collected. The compensation may occur simultaneously with pressure information collection and/or electrodermal activity reading capture. The compensating may be accomplished real time as the electrodermal activity readings are captured.

In addition to electrodermal activity being collected, a sensor may perform evaluation of skin temperature. The flow 700 may include correcting electrodermal activity for skin temperature 740 of the individual. The flow 700 may also include correcting electrodermal activity evaluations based on sensed humidity 750 in the environment.

Figure 8:
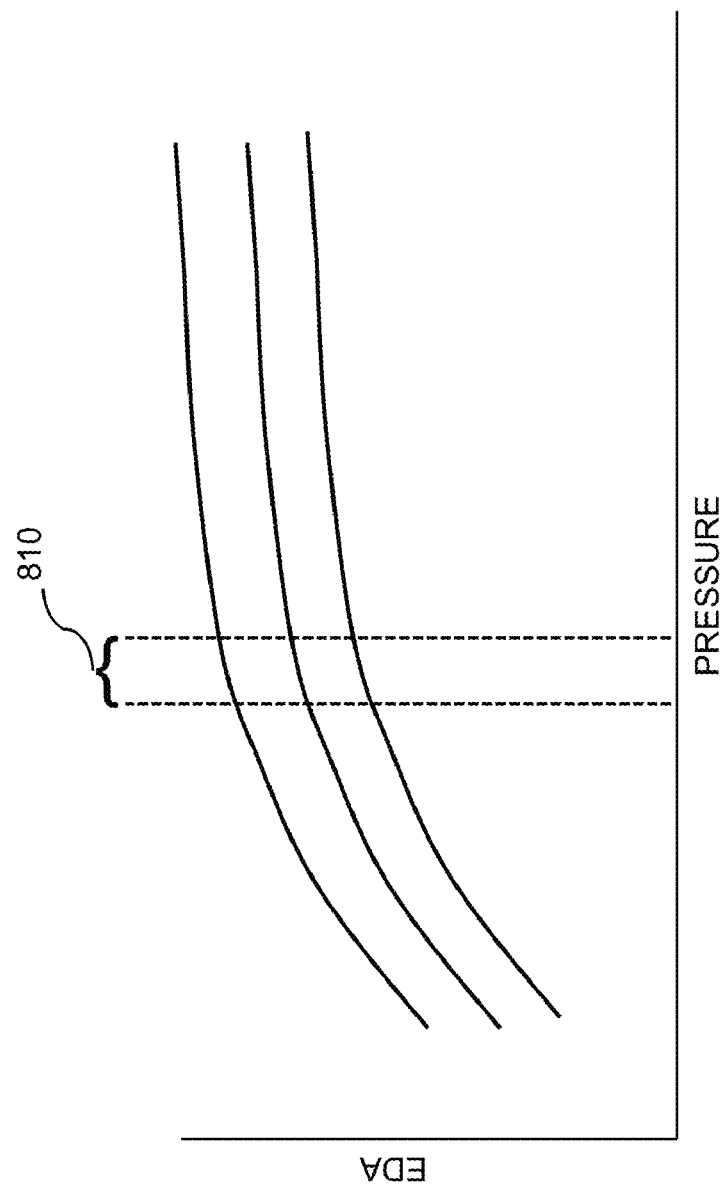
FIG. 8 is a graph illustrating a relationship between pressure and EDA.

The flow 700 may also continue with correcting skin temperature evaluation for the force 760 applied to the electrodes. In some embodiments, a computer program product may be embodied in a non-transitory computer readable medium that, when executed, performs steps of: capturing electrodermal activity readings from a body to which electrodes are in contact with skin; collecting pressure information on an amount of pressure applied to the electrodes which are in contact with the skin; and compensating the electrodermal activity readings based on the pressure information which was collected. In embodiments, a system for measuring physiology may comprise: a sensor including a pair of electrodes and one or more pressure sensing devices; and a processor attached to the sensor wherein the processor is configured to perform steps of: capturing electrodermal activity readings from skin of a body to which the pair of electrodes are in contact; collecting pressure information on an amount of pressure applied to the electrodes with the one or more pressure sensing devices; and compensating the electrodermal activity readings based on the pressure information which was collected FIG. 8 is a graph illustrating a relationship between pressure and electrodermal activity (EDA). The pressure is shown on the x-axis while the EDA is shown on the y-axis. The units for EDA may be micro-siemens or some other units that describe conductance. The units for pressure may be pounds or grams or some other units that can be associated with force. The graph 800 shows that, generally, as pressure is increased on the electrodes that the EDA is increased. One reason why EDA may increase as a function of pressure is that more of each electrode is in contact with the skin as pressure increases. Another reason why EDA may increase with pressure is that more perspiration may be squeezed from pores in the skin. Another reason the conductance may increase with pressure is that the distance is shortened between the liquid partially filling the sweat glands and the electrode, thereby reducing the amount of resistive material in the path. A recommended pressure range 810 may be chosen as the base pressure around which to normalize EDA. Differing amounts of pressure may need to be compensated for in order to determine a more useful EDA. If more pressure is being applied during a reading than that of the recommended pressure range, compensation will be useful to lower the EDA value. If less pressure is applied during a reading, compensation may be useful to increase the EDA value. Compensation may be accomplished using an equation or by using a look up table. For example, the current pressure and EDA reading might suggest that the pressure and EDA are too high, and these two values, together with adjacent EDA values, could be used to index into the compensation function and to determine how to best adjust the EDA downward. The compensation, and therefore the corresponding equation or look up table, may be different for different types of electrodes. Likewise, the compensation may be different for sensors placed on different parts of the body. For instance, electrodermal activity response may vary for the palm, the wrist, the leg, or other part of the body. Also, the compensation may be different for differing demographics of individuals. For instance, an infant may have differing compensation equations or look up tables, due to the amount of fat under the skin where the electrodes are in contact with the skin.

It will be understood that for each flow chart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, and so on. Any and all of which may be generally referred to herein as a "circuit," "module," or "system."

A programmable apparatus which executes any of the above mentioned computer program products or computer implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random access memory (RAM), a read-only memory (ROM), an erasable programmable read-only memory (EPROM, Flash, MRAM, FeRAM, or phase change memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

It will be appreciated that computer program instructions may include computer executable code. A variety of languages for expressing computer program instructions may include without limitation C, C++, Java, JavaScript, assembly language, Lisp, Perl, Tcl, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described.

While the invention has been disclosed in connection with preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A processor-implemented method for measuring physiology comprising: capturing electrodermal activity readings from a body via electrodes which are in contact with skin; collecting pressure information on an amount of pressure applied to the electrodes by a pressure sensing means, which are in contact with the skin; and compensating the electrodermal activity readings based on the pressure information which was collected.

2. The method according to claim 1 wherein the pressure sensing means comprises one or more of force sensitive resistors, piezoelectric devices, piezoelectric polymers, pressure sensitive materials, and pressure sensitive gels.

3. The method according to claim 1 wherein the compensating is accomplished using one or more of circuitry, a processor, software, and firmware.

4. The method according to claim 1 wherein the compensating is accomplished in real time as the electrodermal activity readings are captured.

5. The method according to claim 1 further comprising correcting electrodermal activity evaluations based on temperature of the skin.

6. The method according to claim 1 further comprising correcting electrodermal activity evaluations based on sensed humidity.

7. The method according to claim 1 further comprising evaluating skin temperature.

8. The method according to claim 7 further comprising compensating skin temperature evaluation based on pressure applied to the electrodes.

9. A computer program product embodied in a non-transitory computer readable medium for measuring physiology, the computer program product comprising: code for capturing electrodermal activity readings from a body via electrodes which are in contact with skin; code for collecting pressure information on an amount of pressure applied to the electrodes by a pressure sensing means, which are in contact with the skin; and code for compensating the electrodermal activity readings based on the pressure information which was collected.

10. The computer program product according to claim 9 wherein the pressure sensing means comprises one or more of force sensitive resistors, piezoelectric devices, piezoelectric polymers, pressure sensitive materials, and pressure sensitive gels.

11. The computer program product according to claim 9 wherein the compensating is accomplished using one or more of circuitry, a processor, software, and firmware.

12. The computer program product according to claim 9 wherein the compensating is accomplished in real time as the electrodermal activity readings are captured.

13. The computer program product according to claim 9 further comprising code for correcting electrodermal activity evaluations based on temperature of the skin.

14. The computer program product according to claim 9 further comprising code for correcting electrodermal activity evaluations based on sensed humidity.

15. The computer program product according to claim 9 further comprising code for evaluating skin temperature.

16. The computer program product according to claim 15 further comprising code for compensating skin temperature evaluation based on pressure applied to the electrodes.

17. A system for measuring physiology comprising: a memory which stores instructions; one or more processors coupled to the memory wherein the one or more processors, when executing the instructions which are stored, are configured to: capture electrodermal activity readings from a body via electrodes which are in contact with skin; collect pressure information on an amount of pressure applied to the electrodes, which are in contact with the skin; and compensate the electrodermal activity readings based on the pressure information which was collected.

18. The system according to claim 17 wherein compensating is accomplished in real time as the electrodermal activity readings are captured.

19. The system according to claim 17 wherein the one or more processors are further configured to correct electrodermal activity evaluations based on temperature of the skin.

20. The system according to claim 17 wherein the one or more processors are further configured to correct electrodermal activity evaluations based on sensed humidity.

* * * * *